(12) United States Patent
Kuhns et al.

(10) Patent No.: US 7,785,348 B2
(45) Date of Patent: Aug. 31, 2010

(54) DEVICES AND METHODS OF LOCKING AND CUTTING A SUTURE IN A MEDICAL PROCEDURE

(75) Inventors: Jesse J. Kuhns, Cincinnati, OH (US); Christopher Paul Swain, London (GB); Charles Alexander Mosse, London (GB); Omar J. Vakharia, Mason, OH (US); Rudolph H. Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1511 days.

(21) Appl. No.: 11/127,515

(22) Filed: May 12, 2005

(65) Prior Publication Data

US 2005/0277957 A1 Dec. 15, 2005

Related U.S. Application Data

(60) Provisional application No. 60/571,117, filed on May 14, 2004, provisional application No. 60/571,119, filed on May 14, 2004, provisional application No. 60/571,000, filed on May 14, 2004.

(51) Int. Cl.
*A61B 17/04* (2006.01)
(52) U.S. Cl. ...................... 606/232; 606/148
(58) Field of Classification Search ................. 606/232, 606/74, 103, 144, 148, 120, 157, 158; 24/115 G, 24/135 N, 136 R, 136 I, 115 F
See application file for complete search history.

(56) References Cited

U.S. PATENT DOCUMENTS

| | | | |
|---|---|---|---|
| 3,323,208 A * | 6/1967 | Hurley, Jr. | .................. 606/120 |
| 5,373,840 A * | 12/1994 | Knighton | .................... 606/157 |
| 5,417,700 A * | 5/1995 | Egan | .......................... 606/144 |
| 5,527,341 A | 6/1996 | Gogolewski et al. | |
| 5,584,840 A | 12/1996 | Ramsey et al. | |
| 5,669,917 A | 9/1997 | Sauer et al. | |
| 5,902,321 A | 5/1999 | Caspari et al. | |
| 6,126,677 A * | 10/2000 | Ganaja et al. | ............... 606/232 |
| 6,387,104 B1 | 5/2002 | Pugsley, Jr. et al. | |
| 6,648,903 B1 | 11/2003 | Pierson, III | |

* cited by examiner

*Primary Examiner*—Julian W Woo

(57) ABSTRACT

Devices and methods are provided which may be used for suturing, including performing a totally transoral surgical procedure, such as a posterior gastropexy procedure. A suture lock and cut assembly is provided to lock and cut one or more sutures in one motion, which motion can be a non-curved, non rotational linear motion. The suture lock and cut assembly with one or more sutures threaded therethrough may be pushed through, for example, a patient's esophagus and into the stomach by the tip of an endoscope, or alternatively, sized to be fed through the working channel of the endoscope.

7 Claims, 11 Drawing Sheets

DEVICES AND METHODS OF LOCKING AND CUTTING A SUTURE IN A MEDICAL PROCEDURE

CROSS-REFERENCES TO RELATED APPLICATIONS

This application claims priority to and incorporates by reference the following applications: U.S. Provisional Application 60/571,117 filed May 14, 2004; U.S. provisional Application 60/571,119 filed May 14, 2004; and U.S. Provisional Application 60/571,000 filed May 14, 2004.

FIELD OF THE INVENTION

This invention relates to an endoscopic suturing device. More particularly, this invention relates to an endoscopic suturing device which can perform the dual function of locking onto and cutting the suture.

BACKGROUND

Application of sutures in the gastrointestinal tract is required for several different types of medical procedures, for example, for transoral endoscopic valvuloplasty for gastroesophageal reflux disease (GERD), gastroplasty, fundoplication, anterior gastropexy, posterior gastropexy, suturing esophageal perforations, or closure of the esophageal side of the tracheo-esophageal fistula. Traditionally, these procedures are performed by physicians, such as gastroenterologist or surgeons, either by laparoscopy or open surgical techniques. Such procedures are invasive, as laparoscopy requires that small access incision(s) be made in the body of the patient through which a laparoscope and other surgical enabling tools are provided, while open surgical techniques are traditionally invasive and can have complications and cause long patient recovery periods.

The solution to these problems is to perform these medical procedures through the gastroesophageal tract via the mouth or other naturally occurring orifice. Already available flexible endoscopes, commonly called gastroscopes, can be provided through the gastroesophageal tract and enable illumination and visualization of tissue along the gastroesophageal tract on a video display for diagnostic purposes. These flexible endoscopes also provide an instrumentation means for applying sutures in tissue, such as in the wall of the stomach. What is needed are improved methods of providing a totally transoral surgical procedure, such as a posterior gastropexy procedure, and thereby avoid more-invasive laparoscopic procedures.

New endoscopic suturing methods performed through the gastroesophageal tract as an alternative to the invasive laparoscopic method of, for example, a posterior gastropexy procedure, are currently being developed. For example, suturing methods under the control of endoscopic ultrasound (EUS) are being evaluated. EUS is a procedure that combines endoscopy and ultrasound. In particular, a Mar. 14, 2003 publication authored by Fritscher-Ravens, Mosse, Mukherjee, Yazaki, Park, Mills, and Swain, entitled, "Transgastric gastropexy and hiatal hernia repair for GERD under EUS control: a porcine model," (American Society for Gastrointestinal Endoscopy) describes how endoluminal operations for gastroesophageal reflux are currently limited by the inability of the surgeon to visualize and manipulate structures outside the wall of the gut. The publication describes a way to define the EUS anatomy of structures outside the gut that influence reflux, to place stitches in the median arcuate ligament, to perform posterior gastropexy, and to test the feasibility of crural repair, under EUS control, in pigs. More specifically, by using a linear-array EUS, the median arcuate ligament and part of the right crus were identified and punctured with a needle, which served as a carrier for a tag and suture. These were anchored into the muscle. An endoscopic sewing device was used, which allowed stitches to be placed through a 2.8-mm accessory channel to any predetermined depth.

The publication also describes new methods of knot tying and suture cutting through the 2.8-mm channel of the EUS. More specifically, stitches were placed through the gastric wall into the median arcuate ligament, and one stitch was placed just beyond the wall of the lower esophageal sphincter. The stitches were tied together and locked against the gastric wall, and the surplus length of suture material was then cut and removed. While this publication describes a suitable transgastric gastropexy and hiatal hernia repair procedure, further improvements in methodology and equipment to perform such procedures would be beneficial. For example, the publication describes a process for locking and cutting the suture from inside the stomach. However, the suture requires that a separate suture cutting step, along with its associated cutting instrumentation, be available via the working channel of the endoscope. This may result in multiple passes of instrumentation back and forth through the working channel of the endoscope. What is needed is a way to both lock and cut a suture automatically with a single device and thereby simplify the medical procedure, such as a posterior gastropexy procedure.

It is therefore an object of the invention to provide improved methods of performing a totally transoral surgical procedure, such as a posterior gastropexy procedure, and thereby avoid more-invasive laparoscopic procedures.

It is another object of this invention to provide a single mechanism for locking and/or cutting a suture and thereby simplifying medical procedures, such as, but not limited to, a posterior gastropexy procedure.

SUMMARY OF THE INVENTION

Certain embodiments of the present invention are directed to providing improved methods of performing a totally transoral surgical procedure, such as a posterior gastropexy procedure, and thereby avoiding more-invasive laparoscopic procedures. Several embodiments of the present invention provide a device and method for a physician in a medical procedure to automatically lock and cut a suture in one motion and without the need for additional cutting instrumentation, rather than perform separate locking and cutting actions.

In one embodiment of the invention, a suture lock and cut assembly is provided that forms a hollow body that is slidably connected upon a stem through which one or more sutures is threaded. Depending on the slidable position of the body upon the stem, a locking arm is first engaged to clamp the suture permanently within the stem, and a cutting arm is engaged next to cut any surplus suture, which is then removed from the patient.

In another embodiment of the invention, a suture lock and cut assembly is provided that forms a hollow body, within which a clamp device is engaged and through which a suture is threaded. Depending upon the slidable position of the clamp device within the body, first, the suture within the clamp device is engaged to clamp the suture permanently, and then a cutting knife is engaged to cut any surplus suture, which is then removed from the patient.

While the suture lock and cut assembly may be sized to be introduced through an endoscopic instrument, in some applications the suture lock and cut assembly with one or more sutures threaded therethrough can be pushed through, for example, a patient's esophagus and into the stomach, by the tip of an endoscope, in the event the suture lock and cut assembly is sized to not fit through the working channel of the endoscope.

BRIEF DESCRIPTION OF THE DRAWINGS

While the novel features of the invention are set forth with particularity in the appended claims, the invention, in all its embodiments, may be more fully understood with reference to the following description and accompanying drawings.

DETAILED DESCRIPTION OF THE INVENTION

Figure 1:
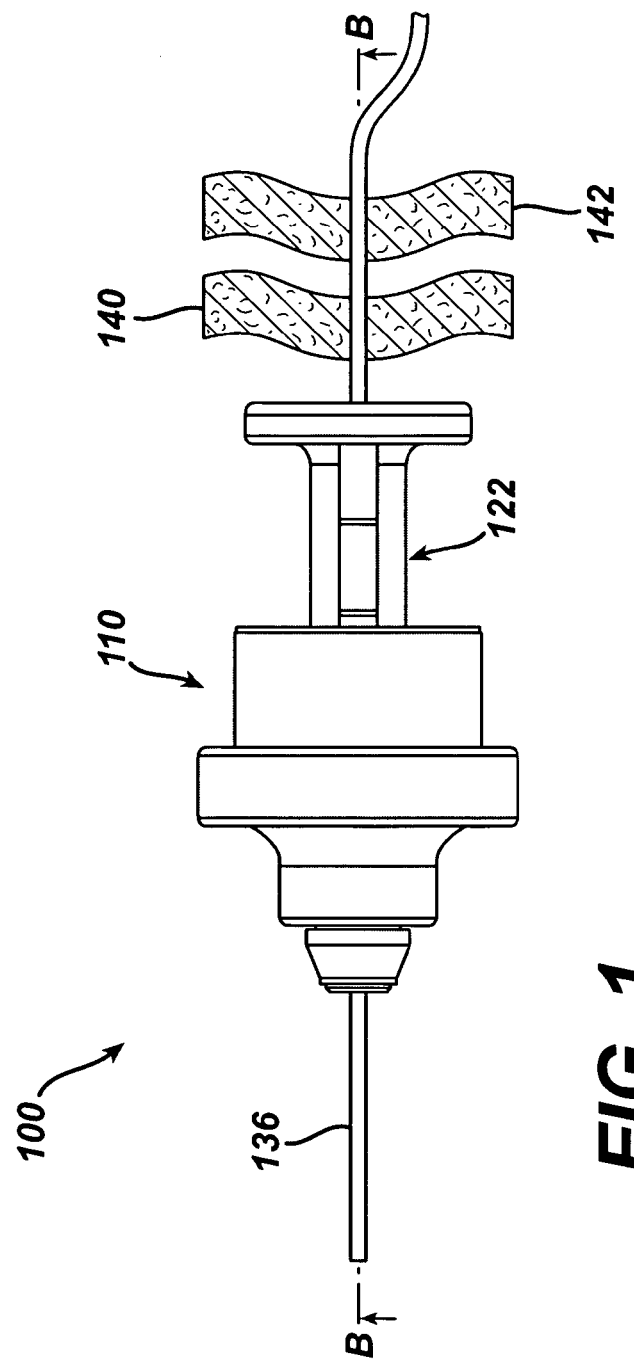
FIG. 1 illustrates a side view of a suture lock and cut assembly in accordance with a first embodiment of the invention.

FIG. 1 illustrates a side view of a suture lock and cut assembly 100 in accordance with a first embodiment of the invention. Suture lock and cut assembly 100 includes a body 110 that is installed upon a stem 122. FIG. 1 shows suture lock and cut assembly 100 in use and, therefore, it includes a suture 136, which runs through the center of suture lock and cut assembly 100 and attaches together a first tissue 140 and a second tissue 142. Suture lock and cut assembly 100 is not limited to a single suture 136 installed therein, a plurality of sutures 136 may be engaged within a single suture lock and cut assembly 100. Further details of suture lock and cut assembly 100, in combination with suture 136, first tissue 140, and second tissue 142, are found in reference to FIGS. 2 through 6.

Figure 2:
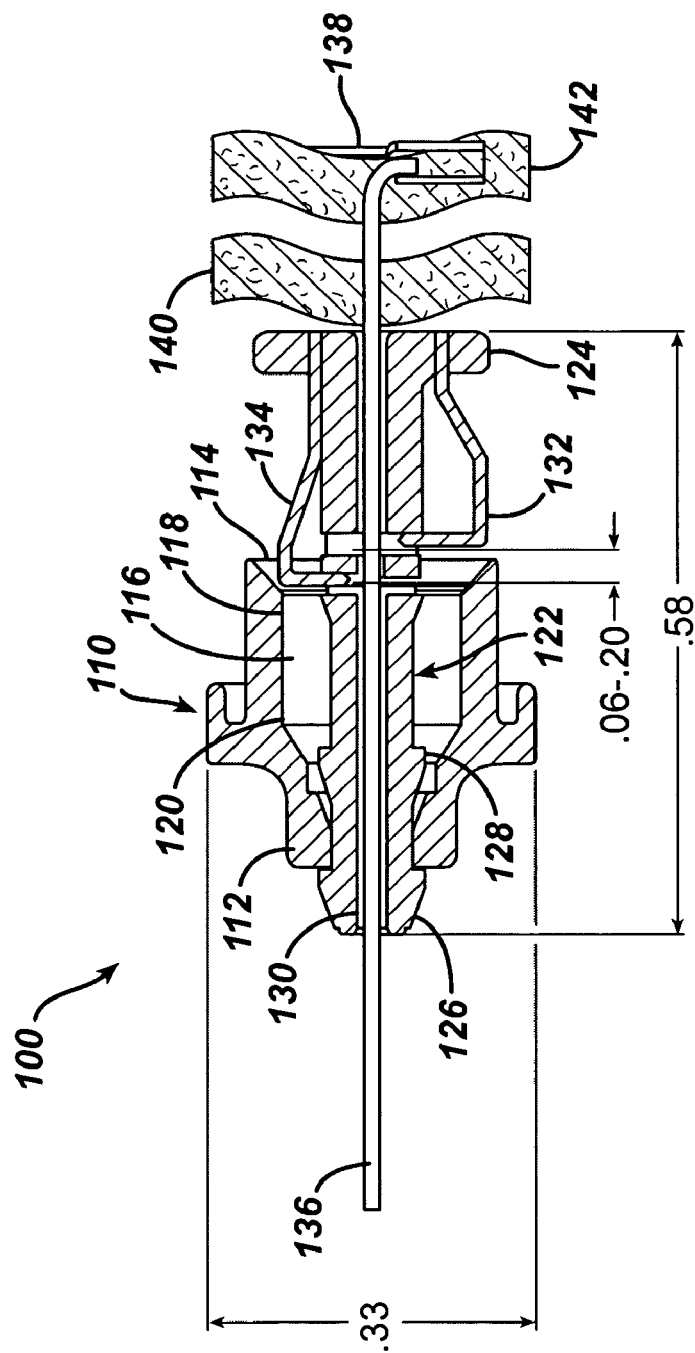
FIG. 2 illustrates a cross-sectional view of the suture lock and cut assembly of the first embodiment of the invention, in the default state, taken along line B-B of FIG. 1.

FIG. 2 illustrates a cross-sectional view of suture lock and cut assembly 100 taken along line B-B of FIG. 1 in accordance with a first embodiment of the invention. Suture lock and cut assembly 100 can include body 110, which as a first end 112 and a second end 114. Body 110 is hollow and has openings at both ends; therefore, it includes a cavity 116 along its full length. The geometry of body 110 and cavity 116 is irregular, as shown in FIG. 2. More specifically, body 110 and cavity 116 are largest in size nearest second end 114 and tapered to a smaller size nearest first end 112. Accordingly, cavity 116 includes a clearance surface 118, which is oriented toward second end 114 and a tapered surface 120, which is oriented toward first end 112.

Inserted through cavity 116 of body 110, suture lock and cut assembly 100 can further comprise stem 122, which has a stem base 124, which, when installed, is oriented toward second end 114 of body 110. At the end of stem 122, opposing stem base 124 is a pair of raised structures spaced some distance apart that form a first barb 126 and a second barb 128. The geometry of cavity 116 nearest first end 112 of body 110 matches the geometry of first barb 126 and second barb 128. Running within stem 122 along its full length is a channel 130, as shown in FIG. 2.

Suture lock and cut assembly 100 can further comprise a cantilever-type locking arm 132 and a cantilever-type cutting arm 134, each of which has one end anchored within stem base 124 and an opposing end that passes through slots within the wall of stem 122 and allows their tips to enter channel 130, as shown in FIG. 2. Suture lock and cut assembly 100 performs the dual functions of automatically clamping and cutting suture 136 within one apparent motion by the user, although it is recognized that the clamping and cutting actions are two separate events that occur as body 110 and stem base 124 are compressed.

Body 110 and stem 122 are formed of, for example, molded plastic, whereas locking arm 132 and cutting arm 134 are formed of any suitable metal that is hard, tempered, and possesses spring properties, such as alloy steel. Alternatively, locking arm 132 (but not cutting arm 134) is formed of plastic, such as a polyetheretherketone (PEEK™) polymer material. PEEK is a general name for a series of polymers, i.e., rigid thermoplastic, which is commonly mixed with other resins and fillers.

Upon initial assembly in preparation of use, body 110 and stem 122 are slidably connected as follows. First barb 126 of stem 122 is inserted into cavity 116 of body 110 via the opening at second end 114; subsequently, first barb 126 comes into contact with the walls of cavity 116 that form first end 112 of body 110. Next, sufficient pushing force is applied, which causes the opening at first end 112 of body 110 to expand temporarily, such that first barb 126 passes through the tightly fitted opening. As a result, and in this default state (i.e., undeployed state), the structure of first end 112 of body 110 is slidable along the outer surface of stem 122, and its slidable range is restricted between first barb 126 and second barb 128. More specifically, on one extreme, the slidable range is restricted by a flat surface of first barb 126 that provides a hard stop when it is abutted against the outer surface of first end 112 of body 110 and, on the opposite extreme, by the tapered surface of second barb 128 that provides resistance when it is abutted against the matching tapered walls of cavity 116 at first end 112 of body 110.

TABLE 1

Example dimensions of suture lock and cut assembly 100

| | Example Dimension |
|---|---|
| Body 110 outside diameter | 0.33 inches |
| Stem 122 length | 0.58 inches |
| First barb 126 and second barb 128 outside diameter | 0.15 inches |
| Locking arm 132 and cutting arm 134 tip-to-tip spacing | 0.06-0.20 inches |

Table 1 provides one non-limiting example of dimensions for the suture lock and cut assembly 100. Also shown in FIG. 2 is suture 136, which is attached to a T-tag 138, which is threaded through channel 130 of stem 122 and which passes through first tissue 140 and is anchored in second tissue 142. T-tag 138 is a well-known medical device for anchoring a suture into body tissue. A method of using suture lock and cut assembly 100 in combination with suture 136, T-tag 138, first tissue 140, and second tissue 142 is described in further detail in reference to FIG. 6.

The operation of suture lock and cut assembly 100 for automatically locking and cutting a suture includes a sequential transition from a default state (i.e., undeployed state) to a lock state, a cut state and, finally, a release state (i.e., deployed state).

FIG. 2 shows suture lock and cut assembly 100 in the default state, which is described as follows.

Default state: In the default or undeployed state, body 110 is slidable along the outer surface of stem 122; its slidable range restricted between first barb 126 and second barb 128, as shown in FIG. 2. In this state, locking arm 132 and cutting arm 134 are not engaged within cavity 116 of body 110 and, thus, are in their relaxed state. Consequently, their tips are not in physical contact with suture 136 within channel 130 of stem 122. Thus, suture 136 slides freely along the length of channel 130.

Figure 3:
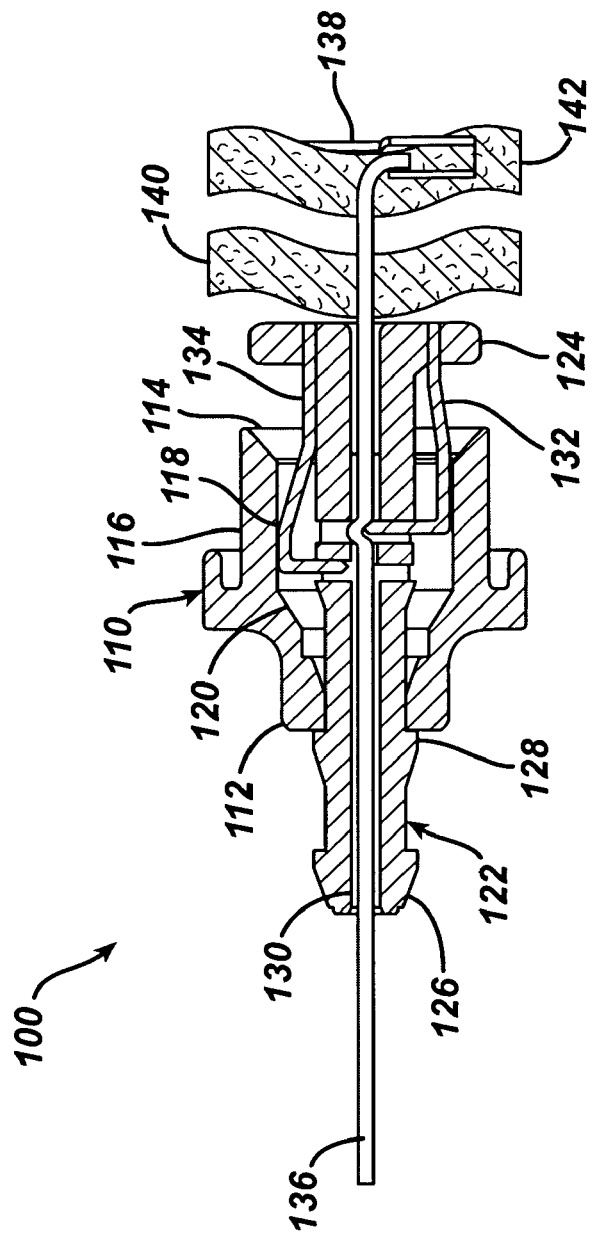
FIG. 3 illustrates a cross-sectional view of the suture lock and cut assembly of the first embodiment of the invention in the lock state.

FIG. 3 illustrates a cross-sectional view of suture lock and cut assembly 100 in the lock state, which is described as follows.

Lock state: The lock state is achieved by the user's applying sufficient pushing force between body 110 and stem 122 to cause the opening at first end 112 of body 110 to expand temporarily, such that second barb 128 of stem 122 passes through the tightly fitted opening. As a result, the structure of first end 112 of body 110 is slidable along the outer surface of stem 122 and its slidable range is now restricted between second barb 128 and stem base 124. More specifically, on one extreme, the slidable range is restricted by a flat surface of second barb 128 that provides a hard stop when it is abutted against the outer surface of first end 112 of body 110 and, on the opposite extreme, by the outer surface of stem base 124 of stem 122 that provides a hard stop when it is abutted against the outer surface of second end 114 of body 110. However, in the lock state, body 110 is positioned such that its first end 112 is abutting second barb 128, and locking arm 132 and cutting arm 134 are engaged within cavity 116 of body 110 because their outer surfaces ride upon clearance surface 118 of cavity 116 but, importantly, without coming into contact with tapered surface 120, as shown in FIG. 3. Consequently, when locking arm 132 and cutting arm 134 are engaged along clearance surface 118 within cavity 116, the position of their tips is forced toward the center of channel 130 of stem 122. In the lock state, locking arm 132 is now in physical contact with suture 136, which is within channel 130 of stem 122, and, thus, provides a clamping action upon suture 136. This is accomplished by locking arm 132 creating a torturous path within stem 122 that prevents suture 136 from sliding freely along channel 130. However, in the lock state, the cutting tip of cutting arm 134 is not in physical contact with suture 136, which is within channel 130 of stem 122.

Figure 4:
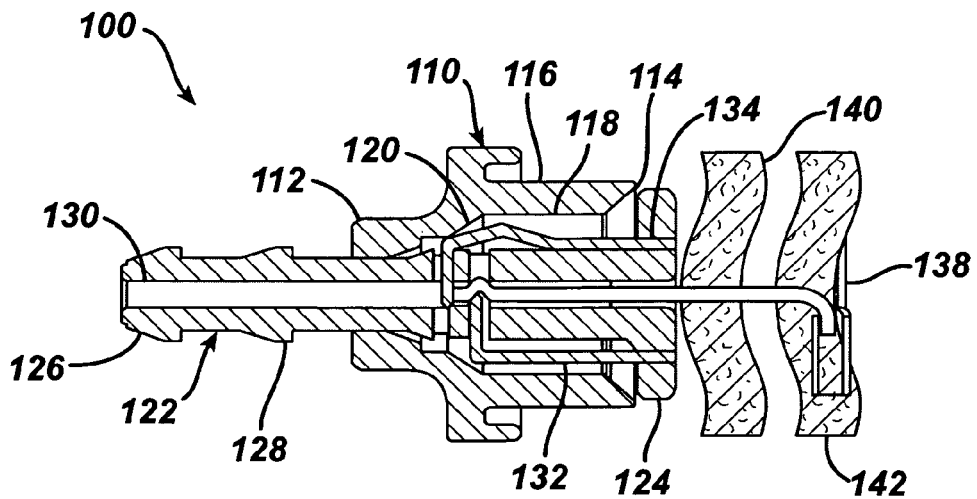
FIG. 4 illustrates a cross-sectional view of the suture lock and cut assembly of the first embodiment of the invention in the cut state.

FIG. 4 illustrates a cross-sectional view of suture lock and cut assembly 100 in the cut state, which is described as follows.

Cut state: The cut state is achieved by the user's sliding body 110 toward stem base 124, such that second end 114 is abutting the outer surface of stem base 124, which causes locking arm 132 and cutting arm 134 to come into contact with tapered surface 120. Consequently, the position of the tips of locking arm 132 and cutting arm 134, which ride upon tapered surface 120 within cavity 116, are forced yet further toward the center of channel 130 of stem 122. In the cut state, locking arm 132 remains in physical contact with suture 136 within channel 130 of stem 122 and, thus, the clamping action is maintained. However, in the lock state, the cutting tip of cutting arm 134 crosses the path of suture 136, which is within channel 130 of stem 122, as shown in FIG. 4 and thereby cuts suture 136 on the side of locking arm 132 that is farthest away from stem base 124.

Figure 5:
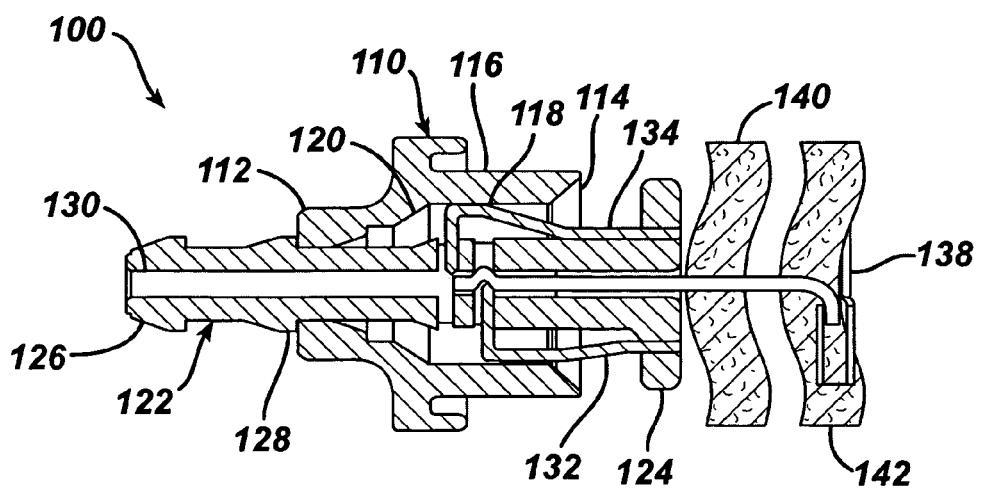
FIG. 5 illustrates a cross-sectional view of the suture lock and cut assembly of the first embodiment of the invention in the release state.

FIG. 5 illustrates a cross-sectional view of suture lock and cut assembly 100 in the release state, which is described as follows.

Release state: In the release state, the user releases pressure upon body 110, which thereby allows locking arm 132 and cutting arm 134 to disengage from tapered surface 120 and allows body 110 to move away from stem base 124, as locking arm 132 and cutting arm 134 are now riding only upon clearance surface 118 of body 110, as shown in FIG. 5. In the release state, locking arm 132 remains in physical contact with suture 136, which is within channel 130 of stem 122, and, thus, the clamping action is maintained indefinitely. The portion of suture 136 exiting stem 122 at first barb 126 is removed, while the portion of suture 136 exiting stem base 124 remains locked within suture lock and cut assembly 100.

Figure 6:
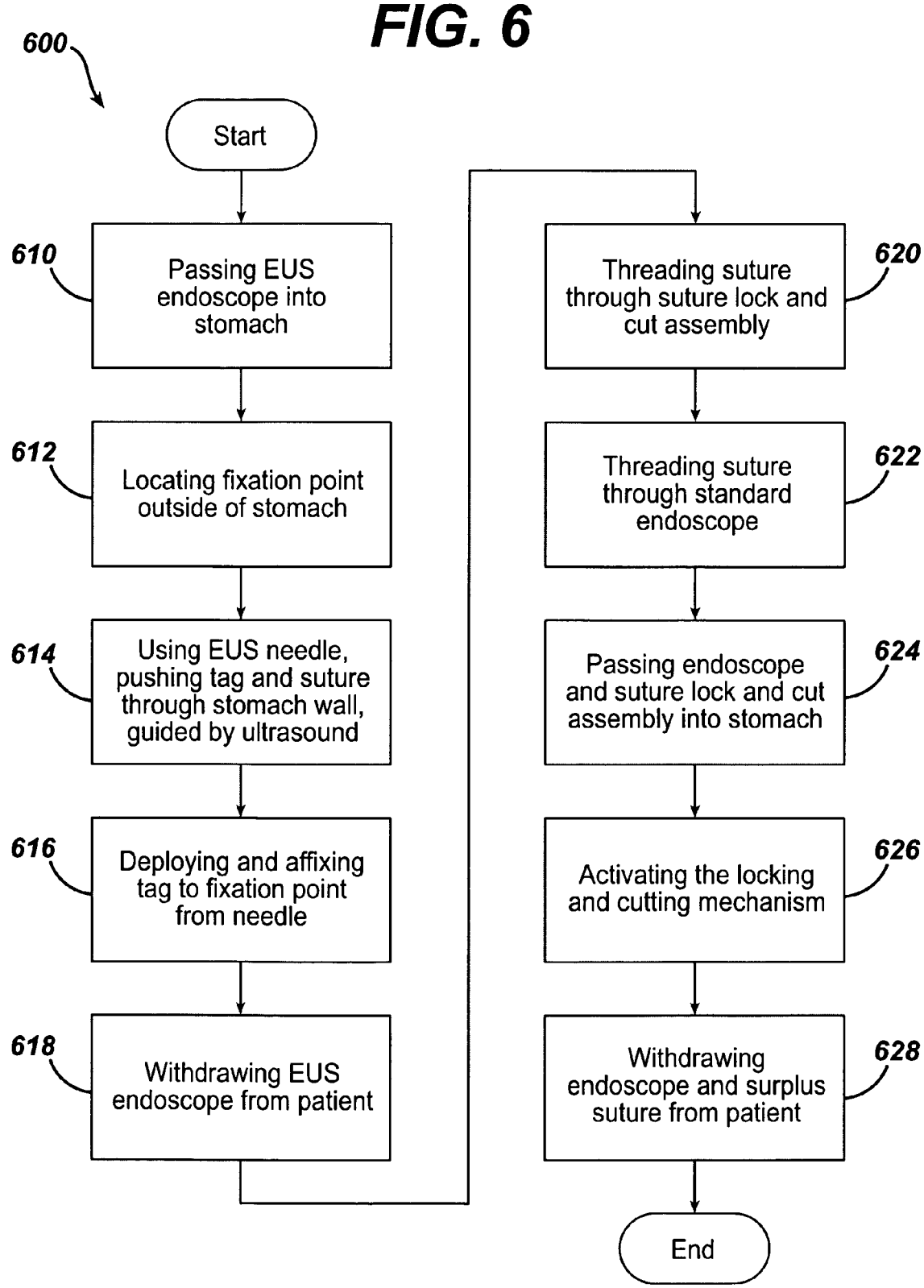
FIG. 6 illustrates a flow diagram of an example method of using the suture lock and cut assembly of the first embodiment of the invention.

FIG. 6 illustrates a flow diagram of an example method 600 of using suture lock and cut assembly 100 in accordance with the invention. More specifically, method 600 provides an example of a posterior gastropexy procedure that uses the suture lock and cut assembly 100 of the present invention. The use of suture lock and cut assembly 100 is not limited to a posterior gastropexy procedure; suture lock and cut assembly 100 may be used in any of various, similar medical procedures. Furthermore, method 600 is not limited to a single suture 136 installed within suture lock and cut assembly 100, a plurality of sutures 136 may be engaged within a single suture lock and cut assembly 100.

At step 610, a physician passes an EUS endoscope through a patient's mouth and esophagus and into the stomach. Example EUS endoscopes include endoscope model GF-UC160P-AT8 manufactured by Olympus Europe (Hamburg, Germany) and endoscope model EG-3630U manufactured by Pentax Medical Company (Orangeburg, N.Y.). The working channel of the EUS endoscope is preloaded with a standard EUS needle, such as is manufactured by Wilson-Cook (Winston-Salem, N.C.), that serves as a carrier for a tag and thread, such as T-tag 138 and suture 136. Suture 136 may run either through the needle or outside the needle, but still inside the working channel of the EUS endoscope; alternatively, suture 136 can run along the outside of the EUS endoscope.

At step 612, under the guidance of the EUS endoscope, the physician locates and identifies structures outside of the stomach wall and selects a fixation point, such as the median arcuate ligament.

At step 614, under the guidance of the EUS endoscope the physician pushes the EUS needle, which is carrying T-tag 138 and suture 136, through the stomach wall, which is represented by first tissue 140 in FIG. 2.

At step 616, under the guidance of the EUS endoscope, the physician deploys and affixes T-tag 138, with suture 136 attached thereto, to the fixation point, such as to the median arcuate ligament, which is represented by second tissue 142 in FIG. 2.

At step 618, the physician withdraws the EUS endoscope and associated instrumentation from the patient, but leaves a length of suture 136 still threaded through the patient's gastroesophageal tract and anchored to second tissue 142 (e.g., median arcuate ligament). The length of suture 136 extends out of the patient's mouth and is accessible to the physician.

At step 620, the physician threads the length of suture 136 that is extending out of the patient's mouth through channel 130 of stem 122 of suture lock and cut assembly 100, which is in the default state, as shown in FIG. 2. Suture 136 is threaded into the stem base 124 end and out of the first barb 126 end of suture lock and cut assembly 100.

At step 622, the physician threads the length of suture 136 that is extending out of the patient's mouth through suture lock and cut assembly 100 and into the working channel of a standard endoscope that has a standard vision system (i.e., not an EUS endoscope). The physician aligns the first barb 126 end of stem 122 into the working channel of the endoscope, such that the tip of the endoscope is abutting first end 112 of body 110. Stem 122 may serve as an alignment aid for aligning body 110 to the tip of the endoscope.

At step 624, while holding tension on suture 136 and with the distal end of the endoscope pushing against suture lock and cut assembly 100, which is external to the working channel of the endoscope, the physician passes the endoscope and suture lock and cut assembly 100 through the patient's mouth and esophagus and into the stomach. Suture lock and cut assembly 100 is sliding freely along suture 136 in the default state, until stem base 124 of stem 122 is firmly abutted against the inside of the stomach wall, which is represented by first tissue 140 in FIG. 2.

At step 626, having determined that the desired geometry change between the stomach and the median arcuate ligament (represented by first tissue 140 and second tissue 142) is achieved and while continuing to hold tension on suture 136, the physician applies sufficient pushing force upon the endoscope, whose distal end is abutting body 110, such that the opening in first end 112 of body 110 slips past second barb 128 of stem 122 in the direction of stem base 124 and thereby engages locking arm 132 and cutting arm 134 within cavity 116 of body 110 by their outer surfaces, which ride, first, upon clearance surface 118, which causes locking arm 132 to clamp against suture 136, and second, upon tapered surface 120 of cavity 116, which causes cutting arm 134 to cut suture 136, as shown in FIGS. 3 and 4.

At step 628, having secured suture lock and cut assembly 100 against first tissue 140 and having cut suture 136, the physician relaxes the pushing force upon the endoscope against body 110. As a result, suture lock and cut assembly 100 relaxes into the release state, while suture 136 remains firmly clamped, as shown in FIG. 5. The physician then withdraws the endoscope and surplus material of suture 136 from the patient. Method 600 ends.

In an alternative embodiment, method 600 uses a single EUS endoscope device that also has a standard vision system. As a result, only one endoscope device is needed throughout the entirety of method 600. In this case, the EUS endoscope device with a standard vision system is passed into the patient at step 610. It is removed at step 618, and a the same EUS endoscope device with a standard vision system is passed into the patient at step 624.

Figure 7:
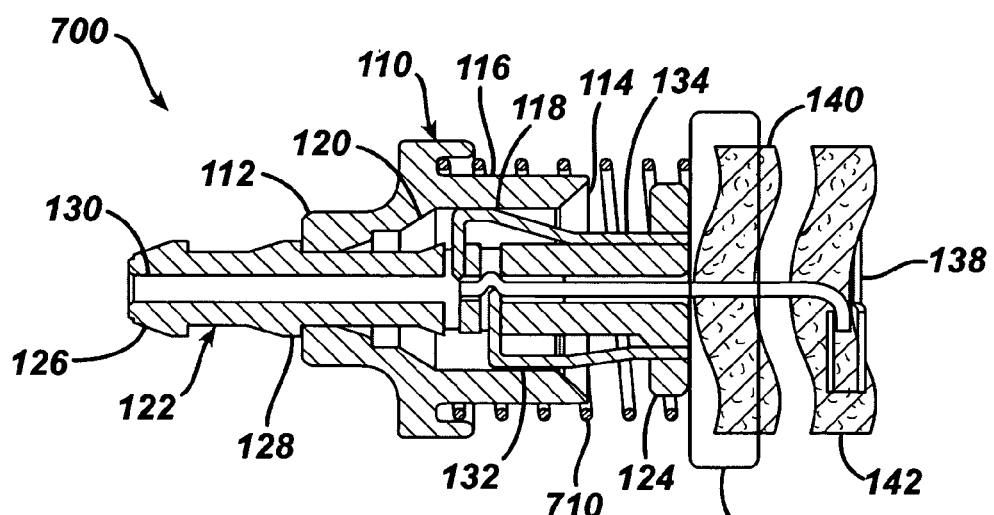
FIG. 7 illustrates a cross-sectional view of a suture lock and cut assembly in accordance with a second embodiment of the invention.

FIG. 7 illustrates a cross-sectional view of a suture lock and cut assembly 700 in accordance with a second embodiment of the invention. Suture lock and cut assembly 700 includes body 110 that is installed upon stem 122, as described in FIGS. 1 through 5. However, suture lock and cut assembly 700 further includes a compression spring 710, which is anchored at one end around the circumference of body 110 and abutted against a pledget 712 at its opposing end, such that it is sandwiched between stem base 124 and first tissue 140. Pledget 712 has a center hole through which suture 136 may pass. Like suture lock and cut assembly 100, suture lock and cut assembly 700 performs the dual functions of automatically clamping and cutting suture 136 within one apparent motion by the user, although it is recognized that the clamping and cutting actions are two separate events that occur as body 110 and stem base 124 are compressed.

Suture lock and cut assembly 700 operates identically to suture lock and cut assembly 100, as described in FIGS. 1 through 6. However, because pledget 712 presses against first tissue 140 under a force provided by compression spring 710, suture lock and cut assembly 700 is useful in medical procedures, such as an anastomosis process, where a stoma, or a hole, is to be formed in the wall of an organ. Because compression spring 710 presses on pledget 712, compression of the tissue is achieved, which is used to create this hole over time.

The pledget can be coated with, formed from, or contain one or more diagnostic or therapeutic agent. For example, the pledget may comprise a composition selected from the group consisting of medicinal agents, drugs, narcotics, pain killers, hemostatic agents, antibacterial agents, antiseptic agents, diagnostic agents, antiviral agents, blood thinning agents, gene therapy agents, tissue growth or tissue healing agents, radiological agents, radio-isotopes, and combinations thereof.

Figure 8:
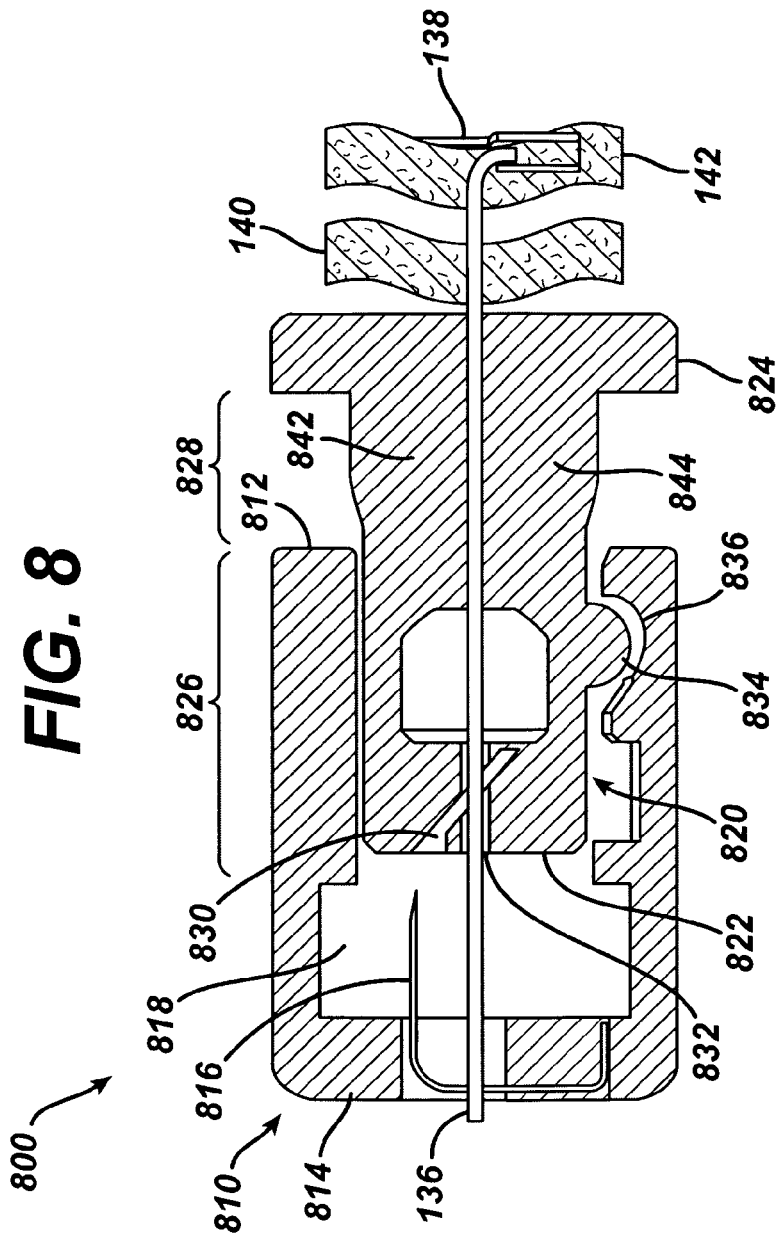
FIG. 8 illustrates a cross-sectional view of a suture lock and cut assembly in accordance with a third embodiment of the invention in the default state.

FIG. 8 illustrates a cross-sectional view of a suture lock and cut assembly 800 in accordance with a third embodiment of the invention. Suture lock and cut assembly 800 includes a body 810, which is installed upon a clamp device 820. FIG. 8 shows suture lock and cut assembly 800 in use and, therefore, it includes suture 136, which runs through the center of suture lock and cut assembly 800 and attaches together first tissue 140 and second tissue 142. Further details of suture lock and cut assembly 800, in combination with suture 136, first tissue 140, and second tissue 142, are found in reference to FIGS. 9 through 12. Also shown in FIG. 8 is suture 136, which is attached to T-tag 138, which is threaded through suture lock and cut assembly 800, passes through first tissue 140, and is anchored in second tissue 142. Suture lock and cut assembly 800 is not limited to a single suture 136 installed therein, a plurality of sutures 136 may be engaged within a single suture lock and cut assembly 800. Like suture lock and cut assembly 100 and 700, suture lock and cut assembly 800 performs the dual functions of automatically clamping and cutting suture 136 within one apparent motion by the user, although it is recognized that the clamping and cutting actions are two separate events that occur as body 810 and clamp device 820 are compressed.

With continuing reference to FIG. 8, suture lock and cut assembly 800 includes body 810, which is a hollow cylindrical shape that has an opening at a body first end 812 that is large enough to accept clamp device 820 therein. Mounted within an enclosed body second end 814 of body 810 is an L-shaped cutting knife 816, which protrudes into a cavity 818 within body 810. Clamp device 820 is cylindrically shaped and has a clamp first end 822 that is sized to fit within the opening at body first end 812 of body 810. Clamp device 820 includes a first side 842 and a second side 844 of clamp device 820 through which suture 136 passes. At the opposite end of clamp device 820 is a clamp base 824 that has an outside diameter that approximates the outside diameter of body 810. Clamp device 820 includes a clamp first region 826 that is nearest clamp first end 822 and that has an outside diameter of 0.16 inches and a clamp second region 828 that is nearest clamp base 824 and that has an outside diameter of 0.17 inches or slightly larger. Included at clamp first end 822 of body 810 is a guide slot 830 and a channel 832. A latching mechanism between body 810 and clamp device 820 is formed by a ball 834, which protrudes from the outer surface of clamp first region 826 and which is fitted within a ball-detent 836, that is formed in the inner wall of body 810, as shown in FIG. 8.

Body 810 and clamp device 820 are formed of any suitably strong, rigid, and nontoxic material, such as molded plastic or stainless steel, whereas cutting knife 816 is formed of any suitable metal that is hard, tempered, and possesses spring properties, such as alloy steel.

Figure 9:
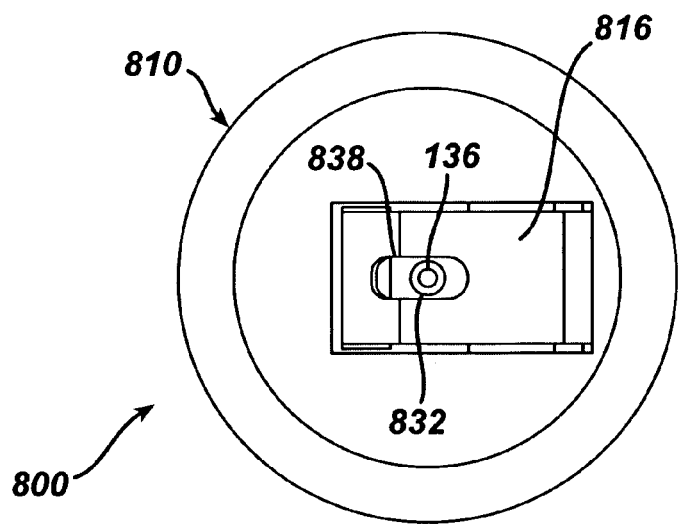
FIG. 9 illustrates a first end view of the suture lock and cut assembly of the third embodiment of the invention.

FIG. 9 illustrates an end view of suture lock and cut assembly 800 from the body 810 end of suture lock and cut assembly 800. In this view, it is shown that cutting knife 816 is a wide flat blade which is mounted within an opening of body second end 814 of body 810. Cutting knife 816 further includes a hole 838. Suture 136 is allowed to pass through body second end 814 of body 810 via hole 838 in cutting knife 816.

Figure 10:
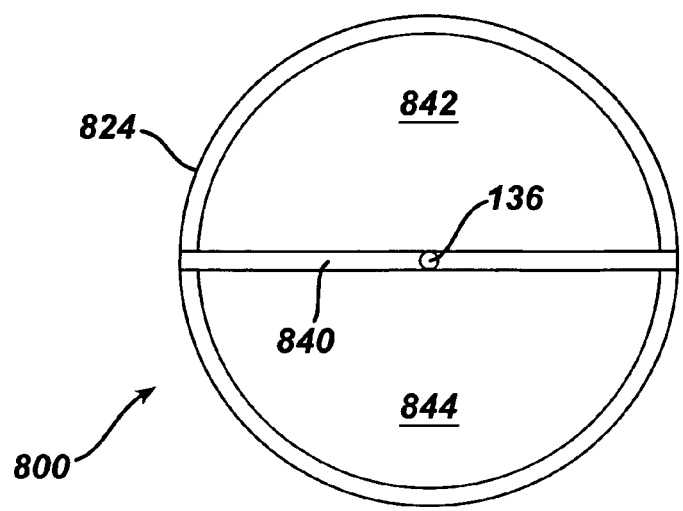
FIG. 10 illustrates a second end view of the suture lock and cut assembly of the third embodiment of the invention.

FIG. 10 illustrates an end view of suture lock and cut assembly 800 from the clamp device 820 end of suture lock and cut assembly 800. In this view, it is shown that suture 136 passes through a slot 840 formed between first side 842 and second side 844 of clamp device 820. When first side 842 and second side 844 of clamp device 820 are in a relaxed state, suture 136 may move freely. Channel 832 allows axial movement but serves to restrain suture 136 from side-to-side movement. By contrast, by squeezing together first side 842 and second side 844 of clamp device 820, suture 136 may be locked in position.

The operation of suture lock and cut assembly 800 for automatically locking and cutting a suture includes a sequential transition from a default state (i.e., undeployed state) to a lock state, a cut state and, finally, a release state (i.e., deployed state).

Again referencing FIG. 8, suture lock and cut assembly 800 is shown in the default state, which is described as follows.

Default state: In the default or undeployed state, body 810 and clamp device 820 are slidably connected as follows. Clamp first end 822 of clamp device 820 is inserted into cavity 818 of body 810 via the opening at body first end 812. Subsequently, ball 834 is aligned with a groove (not shown) that allows ball 834 to be engaged within ball-detent 836, by rotating body 810 relative to clamp device 820. As a result and in this default state (i.e., undeployed state), the slidable movement of clamp device 820 within body 810 is restricted because ball 834 is locked within ball-detent 836, which allows only clamp first region 826 to enter into body 810. In the default state, first side 842 and second side 844 of clamp device 820 are in a relaxed state and suture 136 slides freely within slot 840, along the length of suture lock and cut assembly 800. Because the outside diameter of clamp first region 826 of clamp device 820 is slightly smaller than the inside diameter of body 810, a relaxed state results and, thus, no pressure is applied for squeezing together first side 842 and second side 844 of clamp device 820.

Figure 11:
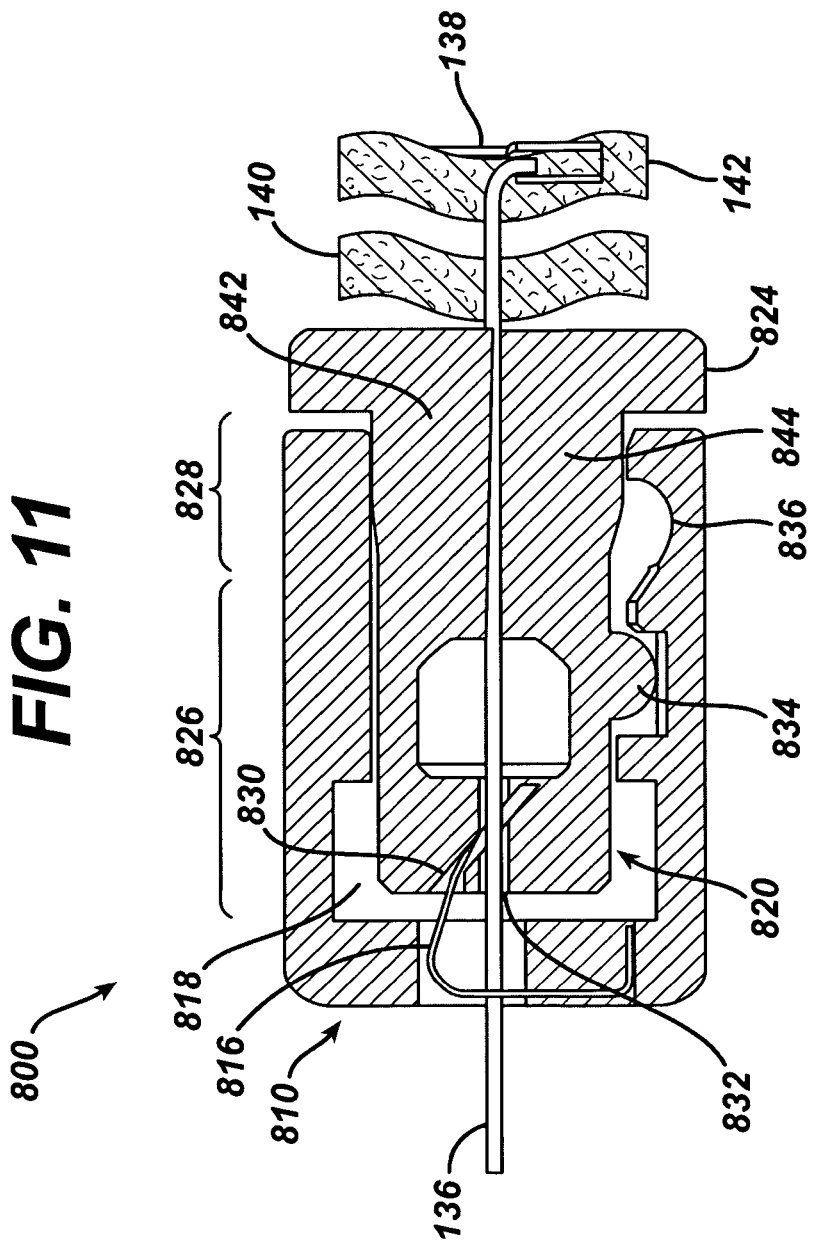
FIG. 11 illustrates a cross-sectional view of the suture lock and cut assembly of the third embodiment of the invention in the lock state.

FIG. 11 illustrates a cross-sectional view of suture lock and cut assembly 800 in the lock state, which is described as follows.

Lock state: The lock state is achieved by the user's applying sufficient pushing force between body 810 and clamp device 820 to cause ball 834 to disengage with ball-detent 836 and slide toward body second end 814 of body 810 and into a clearance area within body 810. As a result, the structure of body first end 812 of body 810 is slidable along the outer surface of clamp second region 828 of clamp device 820. However, in the lock state, body first end 812 of body 810 is not abutting clamp base 824. Because the outside diameter of clamp second region 828 of clamp device 820 is slightly smaller than the inside diameter of body 810, a lock state results and, thus, no pressure is applied for squeezing together first side 842 and second side 844 of clamp device 820. In the lock state, first side 842 and second side 844 of clamp device 820 are now in physical contact with suture 136 within slot 840 of clamp device 820 and, thus, provide a clamping action upon suture 136. This is accomplished by creating a compression zone within clamp base 824 of clamp device 820 that prevents suture 136 from sliding freely along suture lock and cut assembly 800. Additionally, in the lock state, the cutting tip of cutting knife 816 is beginning to enter guide slot 830 of clamp device 820, but it is not in physical contact with suture 136, which is within channel 832 of clamp device 820.

Figure 12:
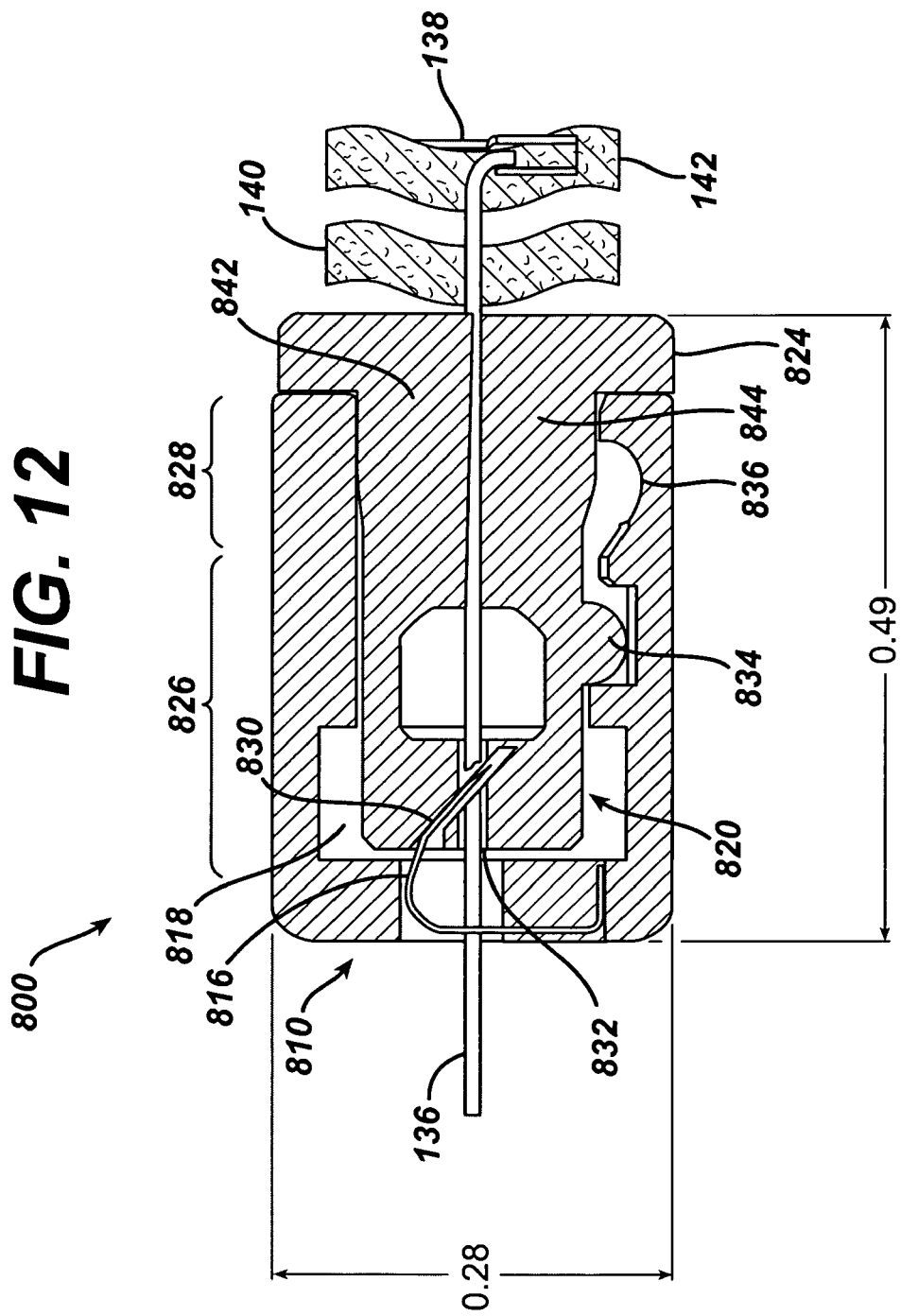
FIG. 12 illustrates a cross-sectional view of the suture lock and cut assembly of the third embodiment of the invention in the cut state.

FIG. 12 illustrates a cross-sectional view of suture lock and cut assembly 800 in the cut state, which is described as follows.

Cut state: The cut state is achieved by the user's sliding body 810 toward clamp base 824 of clamp device 820, such that its body first end 812 is abutting the outer surface of clamp base 824, which causes the cutting tip of cutting knife 816 to ride deeper into guide slot 830, cross the path of suture 136, which is within channel 832, and thereby cut suture 136. In the cut state, first side 842 and second side 844 of clamp device 820 remain in physical contact with suture 136, which is within slot 840 of clamp device 820 and, thus, maintains the clamping action upon suture 136.

Figure 13:
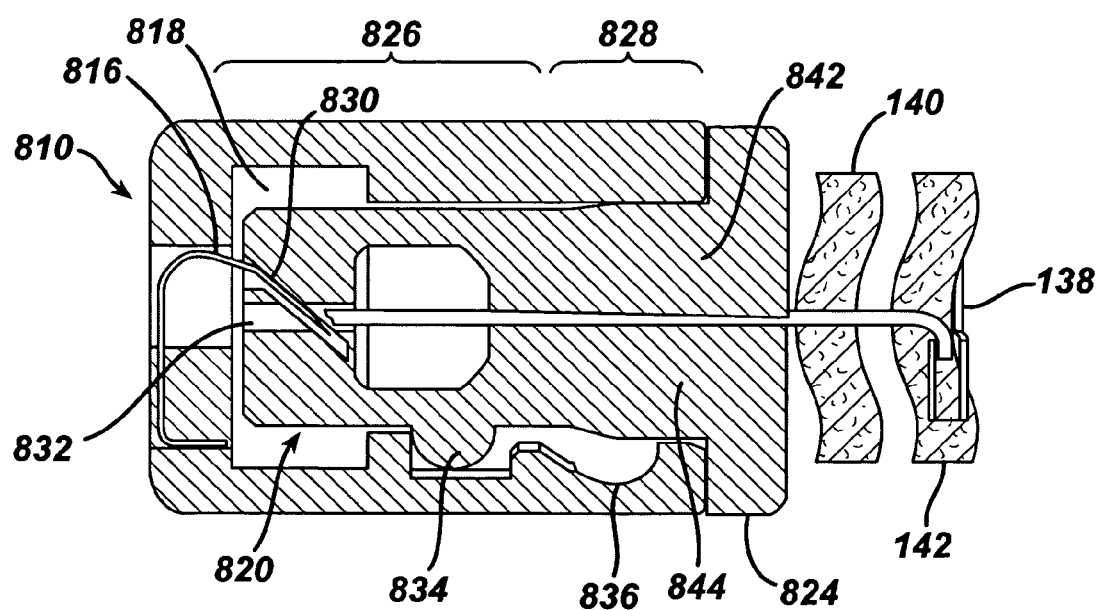
FIG. 13 illustrates a cross-sectional view of the suture lock and cut assembly of the third embodiment of the invention in the release state.

FIG. 13 illustrates a cross-sectional view of suture lock and cut assembly 800 in the release state, which is described as follows.

Release state: In the release state, the user releases pressure upon body 810 and cutting knife 816 remains engaged within guide slot 830 of clamp device 820. In the release state, clamp second region 828 of clamp device 820 remains engaged within body 810 and, thus, pressure is maintained for squeezing together first side 842 and second side 844 of clamp device 820 and, thus, the clamping action is maintained indefinitely. The portion of suture 136 exiting body second end 814 of body 810 is removed, while the portion of suture 136 exiting clamp base 824 remains locked within suture lock and cut assembly 800.

TABLE 2

Example dimensions of suture lock and cut assembly 800

| | Example Dimension |
|---|---|
| Body 810 outside diameter | 0.28 inches |
| Body 810 inside diameter | 0.16 inches |
| Body 810 length | 0.41 inches |
| Clamp device 820 length | 0.34 inches |
| Clamp first region 826 outside diameter | 0.15 inches |
| Clamp second region 828 outside diameter | 0.17 inches |
| Length of suture lock and cut assembly 800 when closed and locked | 0.49 inches |

Table 2 provides a non-limiting example of dimensions of a suture lock and cut assembly 800. By substituting the specific lock and cut mechanisms of suture lock and cut assembly 800, the method of using suture lock and cut assembly 800, in combination with suture 136, T-tag 138, first tissue 140, and second tissue 142, is generally the same as described in FIG. 6, in reference to suture lock and cut assembly 100.

While the present invention has been illustrated by description of various embodiments, it is not the intention of the applicants to restrict or limit the spirit and scope of the appended claims to such detail. Numerous other variations, changes, and substitutions will occur to those skilled in the art without departing from the scope of the invention. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. A surgical suture locking and cutting implant, the implant comprising:
   a body having an internal cavity communicating with openings at both ends of the body; and
   a stem disposed at least partially within the internal cavity, the stem having a channel extending through the length of the stem for receiving suture therethrough;
   wherein the stem and body are slidable with respect to one another from a first position to a second position to provide the functions of holding suture and cutting suture.

2. The implant of claim 1 wherein the stem is slidable to the second position to hold suture.

3. The implant of claim 1 wherein the stem is slidable to the second position to cut suture.

4. The implant of claim 1 wherein the stem is slidable to hold and cut suture.

5. The implant of claim 1 wherein the stem is slidable to hold and cut suture in a single motion.

6. The implant of claim 1 further comprising a suture locking arm for holding suture.

7. The implant of claim 1 further comprising a suture cutting arm for cutting suture.

* * * * *